United States Patent

Rose et al.

Patent Number: 5,246,466
Date of Patent: Sep. 21, 1993

[54] OXIDATION DYES

[75] Inventors: David Rose, Hilden; Edgar Lieske; Horst Hoeffkes, both of Duesseldorf, all of Fed. Rep. of Germany

[73] Assignee: Henkel Kommanditgelsellschaft auf Aktien, Duesseldorf, Fed. Rep. of Germany

[21] Appl. No.: 934,544

[22] PCT Filed: Apr. 2, 1991

[86] PCT No.: PCT/EP91/00629
§ 371 Date: Oct. 9, 1992
§ 102(e) Date: Oct. 9, 1992

[87] PCT Pub. No.: WO91/15188
PCT Pub. Date: Oct. 17, 1991

[30] Foreign Application Priority Data

Apr. 9, 1990 [DE] Fed. Rep. of Germany ....... 4011481

[51] Int. Cl.$^5$ ............................................. A61K 7/13
[52] U.S. Cl. ........................................ 8/407; 8/406; 8/408; 8/409; 8/410; 8/412; 8/414; 8/416; 8/421; 8/423; 424/70
[58] Field of Search ............... 8/406, 407, 408, 409, 8/410, 412, 414, 416, 421, 423; 424/70

[56] References Cited

U.S. PATENT DOCUMENTS

| 4,330,291 | 5/1982 | Bugaut et al. | 8/416 |
| 4,473,374 | 9/1984 | Bugaut et al. | 8/405 |
| 4,797,129 | 1/1989 | Junino et al. | 8/416 |

FOREIGN PATENT DOCUMENTS

| 162625 | 9/1905 | Fed. Rep. of Germany . |
| 276761 | 7/1914 | Fed. Rep. of Germany . |
| 2315256 | 1/1977 | France . |
| 1544127 | 4/1979 | United Kingdom . |
| 2186586 | 8/1987 | United Kingdom . |

OTHER PUBLICATIONS

Jounal of Organic Chemistry, vol. 16, 1951, p. 611.
J. Chem. Soc. Perkin Trans. I, 1988, pp. 1940-1941.

*Primary Examiner*—Paul Lieberman
*Assistant Examiner*—William S. Parks
*Attorney, Agent, or Firm*—Ernest G. Szoke; Wayne C. Jaeschke; Norvell E. Wisdom, Jr.

[57] ABSTRACT

1,3-disubstitued nitrobenzenes of the general formula I:

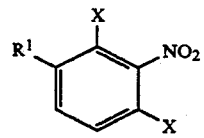

in which X is a hydroxyl group or an amino group and $R^1$ is hydrogen or a $C_{1-4}$ alkyl group and their salts are suitable for use as an oxidation dye precursor of the coupler type, together with prior art primary intermediate components, for the production of oxidation dyes, preferably for the production of hair colorants. With developers of the p-phenylenediamine, p-aminophenol, 2.5-diaminopyridine, and 2,4,5,6-tetraaminopyrimidine types, primarily brown hues with great light stability are formed.

5 Claims, No Drawings

OXIDATION DYES

FIELD OF THE INVENTION

This invention relates to the use of 1,3-disubstituted 2-nitrobenzenes for the production of oxidation dyes, more particularly for the production of hair dyes.

STATE OF THE INVENTION

Oxidation dyes contain oxidation dye precursors in a suitable carrier. The oxidation dye precursors used are primary intermediate compounds which form intensive colors by oxidative coupling with one another or with one or more color modifiers in the presence of atmospheric oxygen. Suitable primary intermediate compounds are, for example, primary aromatic amines containing another free or substituted hydroxy or amino group in the para position or ortho position and also diaminopyridines, heterocyclic hydrazone derivatives, 4-aminopyrazolone derivatives and tetraaminopyrimidines.

The dyes obtainable by coupling of the primary intermediate components with one another are generally unsatisfactory. However, colors of high intensity and brilliance can often be obtained by coupling with phenols or aromatic amines.

Suitable color modifiers are, for example, m-phenylene diamines, m-aminophenols, resorcinols, naphthols and pyrazolones.

One of the most important applications of oxidation dyes is in the coloring of hair. Good oxidation hair dye precursors have to satisfy above all the following requirements: they must produce the required tints in sufficient intensity in the oxidative coupling reaction. In addition, they must be readily absorbable by human hair without excessively staining the scalp. In addition, the dye should be absorbed uniformly, i.e. the more seriously damaged hair ends should not be colored to a greater extent than the less damaged hair roots. The colors produced should show high stability to heat, light and the chemicals used for permanent waving. Finally, the oxidation hair dye precursors should be toxicologically and dermatologically safe.

Although nitrophenols and nitroanilines have certain coloring properties for keratin fibers, they are not normally suitable as color modifiers because the nitro group deactivates the aromatic core for the coupling reaction. The use of resorcinol as a color modifier is known from DEPSS 162 625 and 276 761. However, the light stability properties of oxidation hair colors obtainable with resorcinol are only moderate. m-Phenylenediamine and m-tolylenediamine have also long been used as color modifiers.

DESCRIPTION OF THE INVENTION

However, these color modifiers do not provide natural brown tones with the usual primary intermediate components.

SUMMARY OF THE INVENTION

It has now been found that 1,3-disubstituted nitrobenzenes corresponding to general formula I:

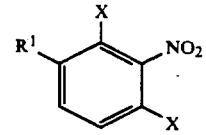

in which X is a hydroxyl group or an amino group and $R^1$ is hydrogen or a $C_{1-4}$ alkyl group, and salts thereof are suitable as color modifiers together with known primary intermediate compounds for producing intensive oxidation colors.

The oxidation colors obtainable in this way are readily absorbed by hair and other keratin fibers and show high stability to light and heat.

DESCRIPTION OF PREFERRED EMBODIMENTS

Accordingly, the present invention also relates to hair dyes containing oxidation dye precursors in a carrier, 1,3-disubstituted nitrobenzenes corresponding to formula I or salts thereof as color modifiers and one or more primary intermediate components typically encountered in oxidation dyes being present as the oxidation dye precursors.

The 1,3-disubstituted nitrobenzenes corresponding to general formula I are compounds known from the literature or may be synthesized by methods known from the literature. 2-Nitroresorcinol is described, for example, in J. Org. Chem. 16 (1951), 611 while 2-nitro-m-phenylene diamine is described in J. Chem. Soc. Perkin Trans. I (1988), 1940–1941. They are suitable as color modifiers for a number of known primary intermediate compounds and produce intensive colors in the form of brown tones. Suitable primary intermediate components are, for example, aromatic amines or phenols containing one or more other $NH_2$ groups, NHR groups or $NR_2$ groups ($R = C_{1-4}$ alkyl) in the para or ortho position, an optionally substituted hydroxyalkyl or aminoalkyl group containing 2 to 4 carbon atoms, o- and p-aminophenol ethers, diaminopyridines, heterocyclic hydrazone derivatives such as for example, 1-methyl-2-pyrrolidone hydrazone, aminopyrazolone derivatives, such as 4-amino-1-phenyl-3-carbamoyl-5-pyrazolone, 2,4,5,6-tetraaminopyrimidine and N-substituted derivatives thereof and 4-hydroxy-2,5,6-tetraaminopyrimidines. Examples of particularly suitable primary intermediate components are given in the following as components D1–D10.

In the hair dyes according to the invention, the compounds corresponding to formula I may be used either in free form or also in the form of a salt. 2-Nitroresorcinols form salts with bases. Suitable salts are, for example, the alkali metal, ammonium, mono-, di- and trialkanolammonium salts containing 2 to 4 carbon atoms in the alkanol group or even the magnesium or calcium salt. 2-Nitro-m-phenylenediamines form salts with acids. Suitable salts are, for example, the hydrochlorides, sulfates, phosphates, acetates, propionates, lactates or citrates.

In addition to the 1,3-disubstituted nitrobenzenes corresponding to formula I, the hair dyes according to the invention may also contain other known color modifiers necessary for modifying the tints and for producing naturallooking tones. Known color modifiers of the type in question are, for example, m-phenylenediamines, 2,4-diaminophenol ethers, bis-(2,4-diaminophenoxy)- alkanes, o- and m-cresol, resorcinol, hydroquinone, pyrogallol, pyrocatechol, α-naphthol, 1,5- or 1,7-dihydroxynaphthalene, 1-phenyl-3-methyl-5-pyrazolone, 1-phenyl-3-amino-5-pyrazolone, 1phenyl-3,5-diketopyrazolidine, 1-methyl-7-dimethylamino-4-hydroxy-2-quinolone or imidazo[1,2a]pyridin-2(3H)-ones.

The 1,3-disubstituted nitrobenzenes corresponding to formula I and the color modifiers additionally used, if any, are generally added to the hair dyes according to the invention in substantially molar quantities, based on the primary intermediate components used. Although it has proved useful to employ molar quantities, there is no disadvantage in using a certain excess of individual oxidation dye precursors so that primary intermediate components and color modifiers may be present in a molar ratio of 1:0.5 to 1:2.

The oxidation dye precursors or substantive dyes otherwise present in the hair dyes do not have to be individual chemical compounds. On the contrary, they may also be mixtures of the modifier and primary intermediate components to be used in accordance with the invention.

To produce the hair dyes according to the invention, the oxidation dye precursors are incorporated in a suitable cosmetic carrier. Such carriers are, for example, creams, emulsions, gels or even surfactant-containing foaming solutions, for example shampoos or other preparations suitable for application to the hair. Typical constituents of such cosmetic preparations are, for example, wetting agents and emulsifiers, such as anionic, nonionic, ampholytic or zwitterionic surfactants, for example soaps, fatty alcohol sulfates, alkanesulfonates, α-olefin sulfonates, fatty alcohol polyglycol ether sulfates, ethylene oxide adducts with fatty alcohols, fatty acids and alkylphenols, sorbitan fatty acid esters and fatty acid partial glycerides, fatty acid alkanolamides and also thickeners such as, for example, methyl or hydroxyethyl cellulose, starch, fatty components such as, for example, fatty alcohols, paraffin oils or fatty acid esters, perfume oils and hair-care additives such as, for example, water-soluble cationic polymers, protein derivatives, pantothenic acid and cholesterol.

A particularly suitable carrier is a gel containing 1 to 20% by weight of a soap, preferably ammonium oleate, or s an oil-in-water emulsion containing 1 to 25% by weight of a fatty component and 0.5 to 30% by weight of an emulsifier from the group consisting of anionic, nonionic, ampholytic or zwitterionic surfactants.

The oxidation dye precursors are incorporated in the carrier in quantities of 0.2 to 5% by weight and preferably in quantities of 1 to 3% by weight, based on the dye as a whole. The content of 2-nitroresorcinol in the hair dyes according to the invention may be between about 0.05 and 10 millimoles per 100 g of the hair dye.

Basically, the color can be oxidatively developed with atmospheric oxygen. However, it is preferred to use a chemical oxidizing agent, particularly when the hair is to be both colored and lightened. Particularly suitable oxidizing agents are hydrogen peroxide or adducts thereof with urea, melamine, or sodium borate and mixtures of such hydrogen peroxide adducts with potassium peroxydisulfate.

A preparation of the oxidizing agent is preferably mixed with the preparation of oxidation dye precursors and carrier immediately before coloring of the hair. The ready-to-use hair-coloring preparation formed should preferably have a pH value of 6 to 10.

In a particularly preferred embodiment, the hair dyes are applied in a mildly alkaline medium. The application temperatures may be in the range from 15° C. to 40° C. After a contact time of about 30 minutes, the hair dye is removed from the hair to be colored by rinsing. The hair is then washed with a mild shampoo and dried. There is no need for washing with a shampoo in cases where a carrier of high surfactant content, for example a coloring shampoo, has been used.

The following Examples are intended to illustrate the invention without limiting it in any way.

EXAMPLES

Hair dyes according to the invention were prepared in the form of a hair-dyeing cream emulsion having the following composition:

| | |
|---|---|
| $C_{12-18}$ fatty alcohol | 10 g |
| $C_{12-14}$ fatty alcohol + 2EO sulfate, Na salt, 28% | 25 g |
| Water | 60 g |
| Primary intermediate (component D1–D10) | 7.5 mmole |
| Color modifier (component M1, M2) | 7.5 mmole |
| $Na_2SO_3$ (inhibitor) | 1.0 g |
| Concentrated ammonia solution | to pH 9.5 |
| Water | ad 100 g |

The constituents were mixed together in this order. After addition of the oxidation dye precursors and the inhibitor, the emulsion was first adjusted to pH 9.5 with concentrated ammonia solution and then made up with water to 100 g.

The color was oxidatively developed with 3% hydrogen peroxide solution as oxidizing agent. To this end, 50 g of hydrogen peroxide solution (3%) were added to and mixed with 100 g of the emulsion.

The dyeing cream was applied to about 5 cm long strands of standardized, 90% grey, but not specially pretreated human hair and left thereon for 30 minutes at 27° C. After dyeing, the hair was rinsed, washed with a normal shampoo and subsequently dried.

The following compounds were used as the primary intermediate components (components D1–D10):

D1: p-phenylenediamine
D2: p-tolylenediamine
D3: 2-chloro-p-phenylenediamine
D4: N-methyl-p-phenylenediamine
D5: N-(2-methoxyethyl)-p-phenylenediamine
D6: N,N-bis-(2-hydroxyethyl)-p-phenylenediamine
D7: p-aminophenol
D8: 2,5-diaminopyridine
D9: 1-phenyl-3-carboxyamido-4-amino-5-pyrazolone
D10: 2,4,5,6-tetraaminopyrimidine.

The following color modifiers were used:
M1: 2-nitroresorcinol
M2: 2-nitro-m-phenylenediamine.

The hair colors obtained are listed in the following Table:

| Hair dye example | Primary intermediate | Modifier | Tint |
|---|---|---|---|
| 1 | D1 | M1 | Dark brown |
| 2 | D2 | M1 | Brown |
| 3 | D3 | M1 | Dark brown |
| 4 | D4 | M1 | Dark violet |
| 5 | D5 | M1 | Dark violet |
| 6 | D6 | M1 | Dark violet |
| 7 | D7 | M1 | medium brown |
| 8 | D8 | M1 | Deer-brown |

-continued

| Hair dye example | Primary | intermediate | Modifier Tint |
|---|---|---|---|
| 9 | D9 | M1 | Grey-magenta |
| 10 | D10 | M1 | Yellow-brown |
| 11 | D2 | M2 | Brown-violet |
| 12 | D10 | M2 | Red-brown |

We claim:

1. A process for the production of oxidation dyes, wherein the improvement comprises the use of 2-nitroresorcinol, its salts, or mixtures thereof as a color modifier together with known primary intermediate components selected from the group consisting of primary aromatic amines, diaminopyridines, heterocyclic hydrazone derivatives, aminopyrazolone derivatives and tetraaminopyrimidines, wherein said color modifier and primary intermediate components are present in quantities of 0.2 to 5% by weight of the total composition.

2. Hair dyes containing a color modifier and one or more primary intermediate components selected from the group consisting of primary aromatic amines, diaminopyridines, heterocyclic hydrazone derivatives, aminopyrazolone derivatives and tetraaminopyrimidines, wherein said color modifier and primary intermediate components are present in quantities of 0.2 to 5% by weight of the total composition in a carrier, wherein the improvement comprises the presence of 2-nitroresorcinol as a color modifier.

3. Hair dyes as claimed in claim 2, primary intermediate and color modifier in a molar ratio of 1:0.5 to 1:2, and 2-nitroresorcinol in a quantity of 0.05 to 10 millimoles per 100 g of the hair dye.

4. Hair dyes as claimed in claim 3, wherein the carrier is a gel containing 1 to 20% by weight of a soap or an oil-in-water emulsion containing 1 to 25% by weight of a fatty component and 0.5 to 30 % by weight of an emulsifier selected from the group consisting of anionic, nonionic, ampholytic, or zwitterionic surfactants.

5. Hair dyes as claimed in claim 2, wherein the carrier is a gel containing 1 to 20% by weight of a soap or an oil-in-water emulsion containing 1 to 25% by weight of a fatty component and 0.5 to 30% by weight of an emulsifier selected from the group consisting of anionic, nonionic, ampholytic, or zwitterionic surfactants.

* * * * *